United States Patent [19]

Kawahara et al.

[11] 4,242,505
[45] Dec. 30, 1980

[54] S-ADENOSYL-L-METHIONINE COMPOSITIONS AND PRODUCTION THEREOF

[75] Inventors: Toshihisa Kawahara; Goro Motoki, both of Choshi, Japan

[73] Assignee: Yamasa Shoyu Kabushiki Kaisha, Japan

[21] Appl. No.: 929,294

[22] Filed: Jul. 28, 1978

[30] Foreign Application Priority Data

Aug. 3, 1977 [JP] Japan ................................. 52-92552
Oct. 12, 1977 [JP] Japan ................................ 52-121535
Dec. 30, 1977 [JP] Japan ................................ 52-158856
May 25, 1978 [JP] Japan .................................. 53-61597

[51] Int. Cl.³ ............................................. C07H 19/16
[52] U.S. Cl. ...................................... 536/26; 424/180; 536/24; 536/23
[58] Field of Search ................................... 536/26, 24

[56] References Cited

U.S. PATENT DOCUMENTS

| 3,954,726 | 5/1976 | Fiecchi | 536/26 |
| 4,057,686 | 11/1977 | Fiecchi | 536/26 |
| 4,109,079 | 8/1978 | Kawahara et al. | 536/26 |

Primary Examiner—Johnnie R. Brown
Attorney, Agent, or Firm—Wenderoth, Lind & Ponack

[57] ABSTRACT

S-adenosyl-L-methionine compositions stabilized against decomposition of S-adenosyl-L-methionine comprising S-adenosyl-L-methionine, a sulfuric acid equivalent and a nucleoside sulfate, which are produced from a solution comprising the three essential components in an aqueous solvent by, for example, adding thereto a water-miscible organic solvent thereby to precipitate the composition (process A) and/or by evaporating the aqueous solvent off the solution (process B).

8 Claims, No Drawings

S-ADENOSYL-L-METHIONINE COMPOSITIONS AND PRODUCTION THEREOF

BACKGROUND OF THE INVENTION

1. Field of the Art

This invention relates to S-adenosyl-L-methionine (hereinafter referred to as SAM) compositions comprising SAM, a sulfuric acid equivalent and a nucleoside sulfate (hereinafter referred to as an NS) and especially to the SAM-containing compositions comprising a nucleoside monosulfate (hereinafter referred to an NMS) and/or a nucleoside disulfate (hereinafter referred to as NDS) as the NS component, and to a method for preparation thereof. More specifically, this invention provides a stabilized SAM-containing composition wherein the SAM, which is very unstable in a free form or an ordinary salt form, is stabilized via chemical interaction in the copresence of a sulfuric acid equivalent and an NS.

SAM is a physiological active substance which plays an important role as a methyl group donor of methylation reaction by way of various transmethylases in vivo. For example, SAM is an indispensable substance which serves as the methyl group donor in a transmethylation reaction, e.g., methylation of high molecular substances in vivo such as nucleic acid, protein and fat, formation of creatine from guanidinoacetate, formation of choline from ethanolamine, and the like. Consequently, SAM is useful as a chemotherapeutic agent for metabolic disorders. Its therapeutic value for hepatopias, hyperdislipidemias, generalized or local arteriosclerosis, psychiatric manifestations of depressive and neutrological type, degenerative arythromathies, neurological algetic manifestation, disturbance of the sleeping-making rhythm, etc., has been reported.

From the viewpoint of practical use of SAM in medical drugs, however, SAM is very unstable even at room temperature, and a serious problem has been that SAM alone can hardly be used as a medical drug. Thus, SAM has been prepared in the form of anionic salts such as the iodide, bromide, Reinecke'salt, hydrochloride and sulfate thereof, but all these salts are unstable in storage. For example, dry SAM hydrochloride kept at 37° C. in a dry condition is decomposed to about one-half is initial amount in 4 days.

2. Prior Art

As stabilized SAM salts there have recently been developed p-toluenesulfonate (cf. British Pat. No. 1,425,384); the double salt with p-toluenesulfonic acid and sulfuric acid (cf. U.S. Pat. No. 3,954,726); methanesulfonate, ethanesulfonate, 1-n-dodecanesulfonate, 1-n-dodecanesulfonate, 1-n-octadecanesulfonate, 2-chloroethanesulfonate, 2-bromoethanesulfonate, 3-hydroxypropanesulfonate, camphor-10-sulfonate, 3-bromocamphor-10-sulfonate, cysteinate, benzenesulfonate, lp-chlorobenzenesulfonate, 2-mesitylbenzenesulfonate, 4-biphenylsulfonate, 1-naphthalenesulfonate, 5-sulfosalicylate, p-acetylbenzenesulfonate, 1,2-ethanedisulfonate, o-benzenedisulfonate, chondroitin sulfate, and the double salts with these sulfonic acids and sulfuric acid (cf. U.S. Pat. No. 4,057,686).

Some of these known sulfonates or the double salts with the corresponding sulfonic acids and sulfuric acid, however, are accompanied by problems such as hygroscopic property and unsatisfactory stability and/or the necessity or resorting to complicated processes for their preparation and purification. Moreover, the corresponding sulfonic acids themselves which are contained in these salts are often irritative or poisonous. From the viewpoint of use of SAM as medical drugs, the above-mentioned sulfonates or the double salts with the sulfonic acids and sulfuric acid cannot always be said to be harmless.

SUMMARY OF THE INVENTION

The present inventors have conducted a variety of researches on SAM salts and SAM-containing compositions with consideration of the conditions which satisfy their stability in storage, safety in vivo, productivity on an industrial scale, and the like. As a result, the inventors have found that novel compositions, in which SAM coexists with a sulfuric acid equivalent and an NS and is stabilized via chemical interaction, are optimal forms that satisfy the above-mentioned conditions. The present invention is based on this discovery and further establishment of an industrially applicable process for production of these compositions.

The SAM-containing composition of the present invention (hereinafter referred to as the present composition) comprises SAM, a sulfuric acid equivalent and an NS. The constitution in molar ratio of the composition is preferably SAM: sulfuric acid equivalent: NS = 1: (1 to 3): (0.5 or more), from the viewpoint of the storage stability of SAM contained in the composition, facility of production of the composition, and like factors. The present compositions are generally obtained as white powder, and the SAM contained therein is stable against decomposition for a long period of time at room temperature or higher temperature under dry conditions.

The method for preparation of the present composition having the above-mentioned constitution and properties is not especially restricted, but the preferable methods are classified into the following two processes:

(A) A process comprising contacting an aqueous solution containing SAM, a sulfuric acid equivalent and an NS (hereinafter referred to as the solution of the present composition) with an organic solvent, and then precipitating and collecting the present composition (hereinafter referred to as process (A); and (B) A process comprising distilling away an aqueous solvent from the solution of the present composition to dryness, and collecting the present composition (hereinafter referred to as process (B).

In the present disclosure, the term "aqueous solution" means a solution in water or in a water-hydrophilic organic solvent, and the term "aqueous solvent" means water, a hydrophilic or water-miscible organic solvent or a hydrophilic or water-miscible organic solvent containing water. The terms "hydrophilic" and "water-miscible" are herein used interchangeably.

The nature, utility, and further features of this invention should be apparent from the following detailed description beginning with a consideration of general aspects of the invention and concluding with results of significant tests, specific examples of practice illustrating preferred embodiments of the invention, and reference examples.

DETAILED DESCRIPTION OF THE INVENTION (1) Production of SAM

Production of SAM per se does not comprise any part of the present invention, and any suitable or convenient method of production can be resorted to.

The source and process for preparation of SAM which can be used in the present composition are not especially restricted. For example, the following processes are employed.

(a) Cultivating in a methionine-containing medium the microorganisms belonging to the Saccharomyces, Candida, Hansenula, Mycotorula, Pichia, Debaryomyces, Rhodotorula, Torulopsis, Kloeckera, Cryptococcus, Hanseniaspora, Sporobolomyces, Lipomyces, Trichosporon, Torula, Aspergillus, Penicillium, Rhizopus, Mucor or like, accumulating SAM in the microbial cells and/or in the cultured fluid, subjecting the SAM contained in the microbial cell to extraction with an extractant such as perchloric acid, an acetate ester, a formate ester, trichloroactic acid, hydrochloric acid or sulfuric acid, and then subjecting the SAM in the resulting extract and the cultured fluid as it is to subsequent purification step.

(b) Contacting an aqueous solution containing adenosine triphosphate and methionine with a methionine adenosyltransferase-containing substance such as a soluble enzyme, an enzyme immobilized on a suitable carrier or microbial (dry) cells containing the enzyme to enzymatically synthesize SAM and then subjecting the resulting product to a purification step (for example, refer to Japanese Patent Application No. 71128/1977).

(2) Purification of SAM

The method for purification of an SAM-containing solution from which solid material has been removed such as the cell extract solution, the cultured fluid, or the enzymatic synthesis solution is not especially restricted. The following processes are generally employed.

(a) A process comprising: adjusting the pH of the SAM-containing solution to a value in the range of 3 to 7 contacting the solution with a chelate resin such as Diaion CR 10 (trade name, manufactured by Mitsubishi Kasei Kogyo, K. K., Japan) and Dowex A-1 (trade name, manufactured by Dow Chemical Company, USA), a strongly acidic cation exchange resin such as Dowex 50Wx8 (trade name, manufactured by Dow Chemical Company, USA) and Amberite IR-200 (trade name, manufactured by Rohm & Haas Company, U.S.A.), or a weakly acidic cation exchange resin such as Diaion WK 10 (trade name, manufactured by Mitsubishi Kasei Kogyo K. K., Japan), Amberite IRC-50 and Amberite IRC-84 (trade names, manufactured by Rohm & Haas Company), and Imac Z5 (trade name, manufactured by Shin-etsu Kagaku, K. K., Japan) to adsorb SAM thereonto; fractionally eluting the SAM with an acid solution of a suitable concentration; and obtaining the purified SAM as an SAM salt of the acid used in the elution.

The acids, employed in the elution step include a mineral acid such as hydrochloric acid, sulfuric acid, or nitric acid, a carboxylic acid such as formic acid or acetic acid, a nucleoside sulfate (not required to be the same as the NS contained in the present composition), and an organic sulfonic acid such as p-toluenesulfonic acid. The resulting eluate may be used as it is in the process for preparation of the present composition. However, the eluate is generally treated with a hydrophilic organic solvent such as methanol, ethanol, propanol, acetone, dioxane, methoxyethanol, ethyl ether, or mixtures thereof, or a solution in a hydrophilic organic solvent of phosphotungstate, picric acid, or picrolonic acid to precipitate SAM as a salt, after which the SAM salt is isolated and then used in the preparation of the present composition.

(b) On the other hand, the SAM-containing solution which has not been subjected to the column treatment, is incorporated with the saturated aqueous solution or saturated hydrophilic organic solvent solution of picrolonic acid, and SAM is precipitated selectively as the picrolonate.

(3) Sulfuric acid equivalent

By the term "sulfuric acid equivalent" used in the present invention is meant $H_2SO_4$, $HSO_4^-$ and/or $SO_4^{--}$, which have been typically introduced into the present composition in the case where SAM is used as the sulfate or a solution containing SAM and an NS to which sulfuric acid has been added in preparing the present composition from the solution containing SAM and an NS. The sulfuric acid equivalent may be present as an SAM salt in the present composition in the form of either sulfuric acid, hydrogen sulfate anion or sulfate anion. However, the exact state of its existence is not known at present. Thus, the term "sulfuric acid equivalent" is used in the present invention to represent any of these three species.

(4) Nucleoside sulfates

The nucleoside sulfates (NS) to be utilized in the present invention generally stand for the derivatives of ribonucleoside or deoxyribonucleoside in which the hydroxyl group or groups at the 2'-,3'- and/or 5'-positions (deoxyribonucleoside has no hydroxyl group at the 2'-position) is or are mono- or disulfated.

The sugar moieties of these parent nucleosides, for example, can be pentoses or deoxypentoses; these sugar moieties may have suitable substituents and/or protecting groups, unless these substituted moieties have an adverse effect on the achieving of the objects of the present invention and if they exhibit the effect equivalent to the unsubstituted moiety. Also, the base moieties of these parent nuclosides, for example, can be purine or pyrimidine, and these base moieties may have suitable substituents and/or protecting groups in the same way as in the sugar moieties. Moreover, the free (i.e., not forming an ester with nucleoside) sulfate-hydroxyl group of the nucleoside sulfates can be in the form of functional derivatives such as salts, esters and the like, unless the derivatives have an adverse effect on the achieving of the objects of the present invention.

The nucleoside sulfates will be further described below.

(a) Type of NMS

NMS, which is an example of the NS, is a monosulfate derivative of nucleosies having a purine- or pyrimidine base moiety and sugar moiety of pentose or deoxypentose wherein the hydroxyl group at the 2'-, 3'- or 5'-position has been sulfated. Typical examples of the NMS are the 2'-. 3'- or 5'-monosulfates of a certain natural-type nucleoside or a certain modified nucleoside or mixtures thereof which contribute to stabilization of SAM when they form the present composition with SAM and a sulfuric acid equivalent. Among these, the natural-type nucleosides include inosine, adenosine, guanosine, xanthosine, uridine, cytidine, deoxyinosine, deoxyadenosine, deoxyguanosine, deoxyanthosine, thymidine and deoxycytidine, and the modified nucleosides include the derivatives of these natural-type nucleosides of which the nucleic acid base moieties are substituted with suitable substituents, the typical substituent being an alkyl group such as methyl and ethyl, a halogen such as chlorine, fluorine, iodine and bromine, an acyl group such as formyl, acetyl, propionyl, butyryl, succinyl, benzoyl, an aryl group such as phenyl and tolyl, an aralkyl group such as benzyl and phenetyl, a substituted or unsubstituted amino group such as dimethylamino, diethylamino and amino, an alkoxyl group such as methoxy and ethoxy, or a hydroxyl group.

More specifically, examples of the NMS are inosine-5'-monosulfate, adenosine-5'-monosulfate, guanosine-5'-monosulfate, uridine-5'-monosulfate, cytidine-5'-monosulfate, xanthosine-5'-monosulfate, thymidine-5'-monosulfate, deoxyguanosine-5'-monosulfate, deoxyinosine-5'-monosulfate, inosine-2'(3')-monosulfate, adenosine-2'(3')-monosulfate, guanosine-2'(3')-monosulfate, cytidine-2'(3')-monosulfate, uridine-2'(3')-monosulfate, thymidine -3'-monosulfate, deoxyinosine-3'-monosulfate, deoxyadenosine-3'-monosulfate, deoxyguanosine-3'-monosulfate, and deoxycytidine-3'-monosulfate, which are hereinafter referred to as 5'-IMS, 5'-AMS, 5'-GMS, 5'-UMS, 5'-CMS, 5'-XMS, 5'-TMS, 5'-dGMS, 5'-dIMS, 2'(3')-IMS, 2'(3')-AMS, 2'(3')-GMS, 2'(3')-CMS, 2'(3')-UMS, 3'-TMS, 3'-dIMS, 3'-dAMS, 3'dGMS, and 3'-dCMS, respectively. The NMS which are markedly effective in stabilizing the SAM in the present composition include 5'-IMS, 5'-UMS, 5'-CMS, 5'-GMS, 5'-AMS, 3'-TMS, 2'(3')-AMS, 2'(3')-CMS and 2'(3')-UMS. The purine-deoxynucleoside monosulfates are not always suitable, since they can be readily decomposed at the pH at which the present compositions are prepared.

(b) Type of NDS

NDS, which is another example of the NS, is a disulfate derivative of nucleosides having a purine- or pyrimidine-nucleic acid base moiety and a sugar moiety of pentose or deoxypentose wherein two of the hydroxyl groups at the 2'-, 3'- and 5'-positions have been sulfated. Typical examples of the NDS are the 2'(3'),5'-; 2',3'- or 3',5'-disulfates of certain natural-type nucleosides and certain modified nucleosides, and mixtures thereof which contribute to stabilization of SAM when they form the present composition with SAM and a sulfuric acid equivalent. Among these, the natural-type nucleosides include inosine, adenosine, guanosine, xanthosine, uridine, cytidine, deoxyinosine, deoxyadenosine, deoxyguanosine, deoxyxanthosine, thymidine and deoxycytidine, and the modified nucleosides include the derivatives of these natural-type nucleoside of which the nucleic acid base moieties are substituted with suitable substituents which are the same as those in the case of NMS.

Specific examples of the NDS are inosine-2'(3'),5'-disulfate, adenosine-2'(3'),5'-disulfate, guanosine-2'(3'),5'-disulfate, xanthosine-2'(3'),5'-disulfate, uridine-2'(3'),5'-disulfate, cytidine-2'(3'),5'-disulfate, thymidine-3',5'-disulfate, deoxyinosine-3',5'-disulfate, deoxyadenosine-3',5'-disulfate, deoxyguanosine-3',5'-disulfate, deoxyxanthosine-3',5'-disulfate, deoxycytidine-3',5'-disulfate, adenosine-2',3'-disulfate, inosine-2',3'-disulfate, guanosine-2',3'-disulfate, xanthosine-2',3'-disulfate, cytidine-2',3'-disulfate, and uridine-2',3'-disulfate, which are hereinafter referred to as 2'(3'), 5'-IDS, 2'(3'), 5'-ADS, 2'(3'), 5'-GDS, 2'(3'), 5'-XDS, 2'(3'), 5'-UDS, 2'(3'), 5'-CDS, 3', 5'-TDS,3', 5'-dIDS, 3', 5'-dADS, 3', 5'-dGDS, 3', 5'-dXDS, 3', 5'-dCDS, 2', 3'-ADS, 2', 3'-IDS, 2', 3'-GDS, 2', 3'-XDS 2', 3'-CDS and 2', 3'-UDS, respectively. The NDS which are markedly effective in stabilization of SAM in the present composition include 3', 5'-TDS, 2'(3'), 5'-CDS, 2'(3'), 5'-ADS, 2'(3'), 5'-UDS, 2', 3'-ADS and 2', 3'-UDS. The purine-deoxynucleoside disulfates are not always suitable, since they can be readily decomposed at the pH at which the present compositions are prepared.

(5) Preparation of NMS

NMS is generally prepared synthetically. The process for the synthesis and the method for the purification are not especially restricted in the present invention. Examples of processes are as follows.

(i) In the preparation of various nucleoside sulfates (NS) which comprises reacting a parent nucleoside with a pyrosulfate, a hydrogen sulfate, and/or sulfuric acid in an amide solvent, the reactions are carried out for about 2 to about 3 hours at 0° to 40° C. for preparation of 5'-NMS or at 50° to 100° C. for preparation of 2'- or 3'-NMS. After the reaction is completed, the reaction solution is subjected to adsorption onto an anion exchange resin and then to fractional elution. The eluate comprising the NMS is desalted if desired, concentrated, and then NMS is precipitated therefrom with an organic solvent (cf. Japanese Patent Application No. 47822/1978).

(ii) The parent nucleoside is reacted with triethylamine-N-sulfonic acid in formamide and/or dimethylformamide to selectively snythetize 5'-NMS. Thereafter, purification and separation are carried out in the same way as described above (cf. Japanese Patent Laid-open publication No. 26882/1976).

(iii) The parent nucleoside is reacted with triethylamine-N-sulfonic acid in pyridine solvent to obtain NMS, and thereafter purification and separation are carried out as described above.

(iv) A chloroform solution of chlorosulfonic acid is caused to act on a pyridine solution of the parent nucleoside to synthesize NMS and thereafter purification and separation are carried out in the same way as described above [cf. Bulletin of the Chemical Society of Japan, Vol. 28, No. 9 (1955)].

In this connection, in the non-selective sulfating processes described above, the 2'- or 3'- hydroxyl group of the nucleoside can be selectively sulfated if the 5'-position hydroxyl group is protected with an appropriate protecting group such as trityl, monomethoxytrityl and acyl. The 5'-position hydroxyl group can be selectively sulfated if the 2' and 3'-position hydroxyl groups is protected with an alkylidene group such as isopropylidene group. The deprotection of the protecting group can be carried out in a suitable conventional manner.

(6) Preparation of NDS

In general, NDS is also prepared synthetically. The process for the synthesis and the method for the purification are not especially restricted in the present invention. For example, NDS is prepared according to the above described processes for preparation of NMS wherein the quantity of sulphating agent, the reaction temperature, and the reaction time are adjusted suitably in conformity with the preparation of NDS.

Further examples of processes are as follows. In the process for the preparation of NMS by reacting the parent nucleoside with a pyrosulfate, a hydrogen sulfate, and/or sulfuric acid in an amide solvent, NDS can be synthesized under the conditions of a reaction temperature of 50° to 100° C. and a reaction time of about 6 to about 7 hours (cf. Japanese Patent Application No. 47822/1978). Also, in the process for the preparation of 5'-NMS disclosed in the above mentioned Japanese Patent Laid-open Publication No. 26882/1976, the corresponding NDS can be obtained by prolonging the reaction time for the preparation of each NDS.

In this connection, 2′,3′-NDS can be synthesized if the 5′-hydroxyl group is protected with an appropriate protecting group such as trityl, monomethoxytrityl, or acryl. After the reaction, deprotection of the protecting group can be carried out in a suitable conventional manner.

After the reaction is terminated, purification is conducted by subjecting the resulting reaction mixture to adsorption onto an anion exchange resin, eluting off an NMS fraction, and then eluting an NDS fraction. Thereafter, the same treatments as in the case of NMS are carried out.

(7) Production of the present composition

The present composition can be produced from an aqueous solution of the above-mentioned three essential components by, for example, adding thereto a water-miscible organic solvent thereby to precipitate the composition (process A) and/or evaporating the solvent of the solution (process B).

As the materials for SAM, which is a first component of the present composition, use can be made of SAM in free form or salts, e.g, the hydrochloride, sulfate, phosphotungstate, iodide, bromide, Reinecke's salt, NS salt, organic sulfonates such as p-toluenesulfonate and double salts with an organic sulfonic acid and sulfuric acid; precipitates, dry products and aqueous solutions thereof. When these starting materials are SAM salts other than the sulfate, NS salt or free form thereof, this SAM salt is used in the production of the present invention by contacting an aqueous solution of the SAM salt with a basic anion exchange resin such as Dowex $2 \times 8$ (trade name, The Dow Chemical Company, USA), Amberite IRA-910, Amberite IRA-410 (trade names, manufactured by Rohm & Haas Company), and Diaion SA 20A (trade name, manufactured by Mitsubishi Kasei Kogyo, K. K., Japan), whereby removing the acid radicals from the SAM salt to obtain SAM of a free-base form, or to convert it to the sulfate or NS salt thereof.

As the materials for NS, which is a second component of the present composition, use can be made of the NS of a free acid form or various alkali salt forms. In the case of 5′-AMS, 2′(3′)-AMS, 2′(3′), 5′-ADS, 2′, 3′-ADS, 5′-GMS, 2′(3′)-GMS, 2′(3′), 5′-GDS, 2′(3′)-CMS, 2′(3′), 5′-CDS, 2′, 3′-CDS and 3′,5′-TDS, however, the alkali salt forms thereof are used, since the free acid forms have low solubility in an aqueous acidic solvent. A free acid-form NS having high solubility is preferably used as it is. The NS may be in the form of a solid such as crystals or an aqueous solution when used as the materials of the present composition.

The NS to be used in the present composition is one or more species selected from the group consisting of NMS and NDS described above.

The sulfuric acid equivalent, which is a third component of the present composition, is derived from sulfuric acid which is pure and pharmacologically acceptable.

Examples of methods for preparing an aqueous solution containing these three components, namely the solution of the present composition, are a process comprising dissolving NS and sulfuric acid in an aqueous solution of SAM in a free-form, a process comprising dissolving NS in an aqueous solution of SAM sulfate, and a process comprising adding sulfuric acid in an aqueous solution of NS salt of SAM. The concentrations of each component in the solution of the present composition are determined on the basis of the constitution of the present composition to be produced. Especially when the present composition is obtained according to the above described process (B), the constitution of each component in the aqueous solution results in the constitution of the present composition. The range of concentration of each component in the aqueous solutions [% (W/V)=(solute, g/solution, ml)×100] should be selected to give a suitable ratio of constitution of the present composition, SAM being 3% to 20%, preferably 5% to 10%, NS being 3% to 15%, preferably 5% to 12%, and sulfuric acid equivalent being 1% to 20%, preferably 2% to 10%.

The above described processes (A) and (B) and the like are employed to obtain the present composition from the resulting solution of the present composition.

The process (A) is carried out by contacting the solution of the present composition with 3 to 30 fold volume of an organic solvent to precipitate the present composition. The organic solvent should be miscible with an aqueous solution containing SAM, a sulfuric acid equivalent, and an NS, and the solubility of the present composition therein should be low. Typical organic solvents include: monohydric, dihydric, and trihydric alcohols each having 1 to about 6 carbon atoms such as methanol, ethanol, propanols, tert-butanol, diethylene glycol, and triethylene glycol; a ketone having up to about 4 total carbon atoms such as acetone; an ether or ether alcohol having 2 to about 6 carbon atoms such as dioxane, methoxyethanol and ethyl ether; and mixtures thereof. From the viewpoint of the precipitation yield of the present composition, methanol, ethanol, acetone, a mixture of methanol and acetone (e.g., 1:1), a mixture of ethanol and acetone (e.g., 1:1) and the like are especially preferred.

As for the process (B), in consideration of instability of SAM in a solution state and at a high temperature, the process is carried out by evaporating the aqueous solvent off the solution of the present composition at a lower temperature (not higher than about 35° C., preferably not higher than 30° C.) and in a shorter period of time. For example, a freeze-drying method or a reduced-pressure or vacuum drying method is employed, a freeze-drying method being especially preferred. In the process (B) for obtaining the present composition, the solution of the present composition is preferably prepared by dissolving NS in an aqueous solution of SAM sulfate.

The present composition is thus obtained as a white powder. The present composition contains all of the three components, namely, SAM, a sulfuric acid equivalent, and an NS, so far as it is a solid product in which the three components coexist under chemical interaction. The present composition cannot be produced by simply mixing, e.g., a solid SAM sulfate and a solid NS. In order to produce the present composition, however, it is necessary to prepare an aqueous solution containing each component so that chemical interaction takes place between the respective components and then to obtain the present composition as a precipitate or a dry product from the aqueous solution. The present composition may optionally be in the form of a double salt of SAM, a sulfuric acid equivalent, and an NS in a specific construction ratio of the three components, as one of the states of existence.

The present composition may contain a slight quantity of impurities such as, for example, alkali cations derived from alkali salts of NS and nucleoside trisufates inherent from NS synthesis, in addition to the above-mentioned tree components. In view of stability, the present composition is produced in a dry state which contains preferably not more than 3% and more preferably not more than 1% of moisture.

In general, the present composition is of the following composition.

SAM: 1 mole
Sulfuric acid equivalent: 1 to 3 moles
NS: 0.5 mole or higher

The quantity of NS varies depending on the species of NS used. More specifically, on a basis of the above mentioned quantities of SAM and sulfuric acid equivalent, typical quantities of NS are given below.

In the case of 5'-CMS, effectiveness with respect to stabilization of SAM becomes observable with a quantity 0.7 mole or more, and a remarkable stabilization effect is exhibited with 1 mole or greater quantity. On one hand, in the case of 2'(3'), 5'-UDS, stabilization effect with respect to SAM is observable from a quantity of 0.5 mole or more, and an even more desirable effect is obtained with 1 mole or greater quantity. With regard to the other NS's, their lower limit quantities at which they exhibit effectiveness vary with the type of NS, and it is difficult to set, generally, a critical value thereof, but the desired result can be amply achieved ordinarily with a quantity of 0.7 to 0.8 mole or more, more preferably 1 mole or more.

As described above in detail, in accordance with the method of the present invention, highly stabilized SAM-containing compositions can be provided by utilizing an NS which is a low-toxicity compound.

Typical compositions of the present invention will be described with respect to their stability in storage and preparation by way of examples. These examples are only for illustration and are not intended to limit the scope of the present invention.

In the preservation tests given in the following examples, the percent residual SAM of the present composition and that of the conventional SAM salts were determined by:

taking a predetermined test sample in an ampule, preserving it at 37° or at 50° C. for a specific period of time, dissolving it in distilled water, subjecting a given quantity of the sample solution to a paper-electrophoresis test using 3% acetic acid, subsequently subjecting it to a paper chromatography at right angles to the direction of the electrophoresis using a solvent consisting of ethanol: acetic acid: water (65:1:34) as a developer, detecting the spots of SAM, its decomposition products and NS by means of an ultraviolet detector, eluting the UV-absorbing substances with 0.1 N hydrochloric acid, measuring the optical density of SAM at 260 nm (SAM·$OD_{260}$) and the optical densities of all the ultraviolet-absorbing substances at 260 nm (total $OD_{260}$), calculating percent SAM following the preservation test (SAM %) by the following Equation (1), and then calculating percent residual SAM by the following Equation (2) with the values of the SAM % and percent SAM before the preservation test (SAM % when prepared).

$$\text{SAM \%} = \frac{\text{SAM} \cdot OD_{260}}{\text{total } OD_{260}} \times 100 \quad (1)$$

$$\text{Percent residual SAM (\%)}^* = \frac{\text{SAM \%}}{\text{SAM \% when prepared}} \times 100 \quad (2)$$

* Alternatively, SAM undecomposed (%)

The analysis of the constitution of the present composition was carried out by dissolving a given quantity of the test sample in distilled water, separating the given quantity of the sample solution by two-dimensional development in the same way as described above, detecting the spots of SAM and NS by means of an ultraviolet detector, subjecting the UV-absorbing substances to elution with an eluent of 0.1 N hydrochloric acid, measuring the optical density of SAM at 257 nm and the optical density of each NS at its wavelength of absorption maximum ($\lambda$max), and calculating the molar quantity of each component from the respective molar extinction coefficient ($\epsilon$).

Relation between the constitution of the present composition and stability in storage SAM sulfates were prepared with respectively different molar ratios. Into the resulting aqueous solutions were added and dissolved 5'-CMS and 2'(3'), 5'-UDS respectively in different quantities in terms of molar ratios (based on the number of moles of SAM in the aqueous solution). The resulting solutions were then lyophilized to obtain the present compositions wherein NS selected is 5'-CMS and is 2'(3'), 5'-UDS. The present compositions were subjected to a preservation test for one week at 37° C., and then percent residual SAM in each composition was determined. The results are shown in Tables 1 and 2. Here, the number of moles of SAM in the aqueous solution is that determined by measuring the absorbance of 260 nm and settting the molecular extinction coefficient ($\epsilon$) at 15,400.

TABLE 1

| | Sulfuric acid equivalent/SAM (molar ratio) | | | | | | |
|---|---|---|---|---|---|---|---|
| | 0 | 0.5 | 0.8 | 1.0 | 1.5 | 2.2 | 3.0 |
| 5'-CMS/SAM (molar ratio) 0 | 44.1 | 56.6 | 60.1 | 63.4 | 82.4 | 81.5 | 83.2 |
| 0.5 | 50.1 | 59.9 | 59.1 | 66.5 | 75.5 | 86.6 | 88.7 |
| 0.7 | — | — | — | 82.2 | 89.9 | 90.0 | 92.2 |
| 1.0 | 64.3 | 70.0 | 75.2 | 95.1 | 97.8 | 98.8 | 97.9 |
| 1.5 | — | — | — | 95.3 | 98.8 | 100.2 | — |
| 2.0 | 68.0 | 78.6 | 78.8 | 96.6 | — | 100.1 | 99.9 |
| 2.5 | — | — | — | — | 100.3 | — | 100.2 |
| 3.0 | 72.4 | 81.1 | 80.5 | 96.3 | — | 99.8 | — |
| 5.0 | — | 80.5 | 79.6 | 96.2 | 99.6 | — | 100.4 |

TABLE 2

| | Sulfuric acid equivalent/SAM (molar ratio) | | | | |
|---|---|---|---|---|---|
| | 0 | 0.5 | 1.0 | 1.5 | 3.0 |
| 2'(3'),5'-UDS/SAM (molar ratio) 0 | 44.1 | 56.6 | 63.4 | 82.4 | 83.2 |
| 0.5 | 53.3 | 59.6 | 67.7 | 92.8 | 93.3 |
| 1.0 | 60.1 | 78.5 | 96.6 | 100.2 | 100.1 |
| 1.5 | 69.2 | 73.3 | 98.8 | 97.0 | 101.0 |
| 2.0 | 68.0 | 80.2 | 99.2 | 100.0 | 99.8 |
| 2.5 | 69.8 | 84.4 | 98.1 | 98.1 | 99.2 |
| 3.0 | 72.4 | 85.5 | 100.1 | 99.6 | 100.2 |

As is apparent from Tables 1 and 2, the effects of stabilization are especially remarkable when the ratio of sulfuric acid equivalent/SAM is 1.0 to 3.0, and moreover, that of 5'-CMS/SAM is 0.7 or more, more preferably 1.0 or more, and that of 2'(3'), 5'-UDS/SAM is 0.5 or more, more preferably 1.0 or more, that is, when the constitution of the present composition in molar ratio is SAM: sulfuric acid equivalent: 5'-CMS = 1:(1 to 3):(0.7 or more, more preferably 1.0 or more) and SAM: sulfuric acid equivalent: 2'(3'), 5'-UDS = 1:(1 to 3):(0.5 or more, more preferably 1.0 or more). By the above described production process, a composition wherein sulfuric acid equivalent/SAM is more than 3.0 cannot be produced.

Comparison of stability in storage between the present composition and a mixture prepared by simply mixing solid SAM sulfate and solid 5'-CMS The present composition employed in the above described test (SAM: sulfuric acid equivalent: 5'-CMS=1.0:1.5:2.0) as well as a control sample prepared by mixing a solid SAM sulfate (sulfuric acid equivalent-/SAM=1.5) and a solid 5'-CMS in double the molar quqntity were subjected to the preservation test at 37° C. for specific numbers of days similarly as described above. Thereafter, values of percent residual SAM (%) were determined. The results are shown in Table 3.

TABLE 3

| Preservation days | 3 days | 7 days | 14 days | 30 days |
|---|---|---|---|---|
| The present composition | 100.2 | 100.1 | 99.7 | 99.8 |
| Control | 94.5 | 85.5 | 79.0 | 68.8 |

As indicated in Table 3, the present composition cannot be produced by simply mixing the solid materials of each component. In order to obtain the present composition, it is necessary to prepare an aqueous solution containing the essential components so that chemical interaction will take place between the components thereby to produce the present composition as a precipitate or a dry product from the aqueous solution.

Comparison of stability in storage between the present composition and other SAM salts The present compositions (SAM: sulfuric acid equivalent: 5'-CMS=1.0:1.5:2.0 (5'-CM composition) and SAM: sulfuric acid equivalent: 2'(3'),5'-UDS=1.0:1.5:1.5) and the conventional SAM hydrochloride and SAM sulfate were subjected to the preservation test at 37° C. for specific number of days in the same way as in the preservation test described above, and then determination of their values of percent residual SAM (%) was carried out. The results are shown in Table 4.

TABLE 4

| Preservation days | 7 days | 14 days | 30 days |
|---|---|---|---|
| SAM hydrochloride | 44.1 | 31.4 | 20.2 |
| SAM sulfate | 82.3 | 77.9 | 66.7 |
| 5'-CM composition | 100.1 | 99.7 | 99.8 |
| 2'(3'),5'-UD composition | 101.6 | 98.9 | 100.2 |

As indicated in Table 4, the present compositions exhibit far superior stability in storage in comparison with the conventional SAM salts.

EXAMPLE 1

A commercially available baker's yeast (manufactured by Oriental Kobo Kogyo K.K., Japan) was cultivated in Schlenk's medium [cf. the Journal of Biological Chemistry, Vol. 229, 1037 (1957)] to accumulate SAM therein. The SAM was extracted with 20 liters of 1.5 N perchloric acid from 3.2 kgs of the resulting baker's yeast with accumulated SAM, and thereafter removal of the cell residue was carried out by centrifugation. The extract thus treated was neutralized to pH 5.5 by potassium bicarbonate, and the resulting potassium perchlorate precipitate was removed. Then, 25 liters of the SAM solution thus treated was passed through a column of a chelate resin, Dianion CR 10 (trade name, manufactured by Mitsubishi Kasei Kogyo K.K., Japan) (H+ form) to have SAM adsorbed thereon, followed by elution with 0.01 N hydrochloric acid to obtain 80 liters of the SAM fraction. The eluate was concentrated to 300 ml under reduced pressure, which was then added to a mixed solvent consisting of methanol and acetone (1:1) to obtain 21.0 g of SAM hydrochloride as a precipitate.

The SAM hydrochloride was dissolved in 200 ml of distilled water and then neutralized to pH 7.0 with a strongly basic anion exchange resin, Dowex 2×8 (trade name, The Dow Chemical Company, U.S.A.) (carbonic acid form). Therein were then added and dissolved 20 ml of 12 N sulfuric acid and 29.0 g of 5'-CMS which had been prepared according to Reference example 1 given below, followed by dropwise addition of 2 liters of ethanol. The solution was allowed to cool overnight. The resulting precipitate was filtered and dried at a low temperature to obtain 48.2 g of a preparation of the present composition (94.2% yield).

The preparation was subjected to an elemental analysis and to a two-dimensional development analysis utilizing electrophoresis and paper chromatography in the same way as described above. The constitution (molar ratio) thereof was SAM: sulfuric acid equivalent: 5'-CMS=1.00:1.43:1.21.

The values of the elemental analysis as well as the migration distances, $R_f$ values obtained by the two-dimensional development utilizing electrophoresis (1,000 V, 45 minutes) and paper chromatography and optical densities of SAM and 5'-CMS are as follows. The migration distance (cm.) of electrophoresis is positive for migration toward the cathode side and is negative for migration toward the anode side. This applies to all migration distances set forth hereinafter.

Elemental analysis: C: 33.6%, H: 3.3%, N: 14.5%, S: 12.7%.

Two-dimensional development

| (340 γ of the present composition was spotted) | |
|---|---|
| (distance of migration) | ($R_f$ value) |
| SAM : 9.2 cm/145 min., 1,000 V | 0.35 |
| 5'-CMS : 0.1 cm/145 min., 1,000 V | 0.66 |

Optical density

| | | |
|---|---|---|
| SAM: | $OD_{257}$ = 5.372<br>ε = 14700<br>(in 0.1 N HCl) | : 0.365μ mole |
| 5'-CMS: | $OD_{280}$ = 5.626<br>ε = 12700<br>(in 0.1 N HCl) | : 0.443μ mole |

A certain quantity of the preparation was taken in a 3 ml. ampule and dried under reduced pressure in the presence of phosphorus pentoxide. The preservation test (at 37° C.) was then conducted thereon in the same way as described above, whereupon it was found to be very stable as shown in the following Table.

TABLE 5

| Preservation days | 7 days | 14 days | 30 days |
|---|---|---|---|
| Percent residual SAM (%) | 99.8 | 99.7 | 96.7 |

REFERENCE EXAMPLE 1 (Preparation of 5'-CMS)

In 10 ml of formamide and 5 ml of dimethylformamide was suspended with stirring 2.43 g of cytidine, and 3.64 g of triethylamine-N-sulfonic acid was slowly added thereto. The reaction was continued for 1 hour at room temperature, after which, the reaction mixture was poured into water to terminate the reaction.

The reaction mixture was neutralized to a pH of 6.5 with 1 N sodium hydroxide, then passed through a 200 ml column of Amberite IRA-402 (trade name, Rohm & Haas, U.S.A.) (Cl$^-$ form), and then washed with water. The effluents from the column were combined, adjusted to a pH of 2.5 with 1 N hydrochloric acid, adsorbed on an activated charcoal column, washed with water, and then eluted with 0.02 N sodium hydroxide. The eluate was treated with Diaion PK 216 (trade name, manufactured by Mitsubishi Kasei Kogyo K.K., Japan)(H+ form) to convert 5'-CMS salt to free form, and concentrated. Then a three-fold volume of acetone was added thereto to precipitate crystals. The resulting crystals were dried under vacuum to obtain 2.3 g of cytidine-5'-monosulfate.

EXAMPLE 2

In 40 ml of distilled water was dissolved 4.4 g of SAM hydrochloride obtained in the same way as in Example 1, and thereafter neutralization (pH 7.0) was carried out in the same way as in Example 1. Into the solution were added and dissolved 3 ml of 12 N sulfuric acid and 12.9 g of 5'-CMS obtained according to the process set forth in Reference Example 1. The resulting solution was added dropwise to 200 ml of acetone and allowed to cool overnight. The resulting precipitate was filtered and then dried at a low temperature to obtain 16.3 g of the preparation of the present composition (91.1% yield).

With respect to the preparation, the same analysis and preservation test as in Example 1 were conducted, whereupon the following results were obtained.

Elemental analysis: C: 33.4%, H: 3.8%, N: 14.0%, S: 13.6%.

Optical density
SAM: OD$_{257}$=2.426:0.165 μmole
5'-CMS: OD$_{280}$=4.882:0.384 μmole (Constitution)
SAM: sulfuric acid equivalent: 5'-CMS=1.00:1.05:2.33

(Preservation Stability, 37° C.)

TABLE 6

| Preservation days | 7 days | 14 days | 30 days |
|---|---|---|---|
| Percent residual SAM (%) | 100.1 | 99.9 | 100.3 |

EXAMPLE 3

In 40 ml of distilled water was dissolved 6.5 g of SAM hydrochloride obtained in the same way as in Exmple 1, and then neutralization (pH 7.0) was carried out in the same way as in Example 1. To the resulting solution was added 6 ml of 12 N sulfuric acid, and the resulting solution was added dropwise to 400 ml of acetone, which was then allowed to cool overnight. The resulting precipitate was filtered to obtain 7.4 g of SAM sulfate (yield, 94.8%; sulfuric acid equivalent/SAM=1.50 on the basis of 21.3 m moles of sulfuric acid consumed and 14.2 m moles of SAM).

The SAM sulfate was dissolved in 150 ml of distilled water, and then 4.6 g of 5'-CMS obtained according to the process shown in Reference example 1 was added and dissolved therein. The resulting solution was subjected to freeze-drying (100 μm Hg or lower, shelf temperature 25° C., 10 hours) to obtain 12.0 g of a preparation of the present composition.

With respect to the preparation, the same analysis and preservation test as in Example 1 were conducted. The results were as follows.

(Constitution)
SAM: sulfuric acid equivalent: 5'-CMS=1.00:1.50:1.00

(Preservation Stability, 37° C.)

TABLE 7

| Preservation days | 7 days | 14 days | 30 days |
|---|---|---|---|
| Percent residual SAM (%) | 99.2 | 99.3 | 97.6 |

EXAMPLE 4

In 100 ml of distilled water was dissolved 5.2 g of SAM sulfate obtained in the same way as in Example 3. Into the solution was further added and dissolved 9.7 g of 5'-CMS obtained according to the process described in Reference Example 1. Then, freeze-drying was carried out in the same way as in Example 3 to obtain 14.9 g of a preparation of the present composition.

With respect to the preparation, the same analysis and preservation test as in Example 1 were conducted. The results were as follows.

(Constitution)
SAM: sulfuric acid equivalent: 5'-CMS=1.00:1.50:3.00

(Preservation Stability, (37° C.)

TABLE 8

| Preservation days | 7 days | 14 days | 30 days |
|---|---|---|---|
| Percent residual SAM (%) | 101.2 | 100.2 | 99.7 |

EXAMPLE 5

Example 1 was partially repeated to obtain 21.0 g of SAM hydrochloride as a precipitate.

The SAM hydrochloride was dissolved in 400 ml of distilled water and then neutralized to pH 7.0 with a strongly basic anion exchange resin, Dowex 2×8 (trade name, the Dow Chemical Company, USA) (carbonic acid form). Into the resulting solution were then added and dissolved 20 ml of 12 N sulfuric acid and 58.5 g of 2' (3'),5'-UDS which had been prepared according to the process described in Reference Example 2 set forth below and the solution thus produced was added dropwise to 4 liters of ethanol. The solution thus obtained was allowed to cool overnight. The resulting precipitate was filtered and dried at a low temperature to obtain 47.9 g of a preparation of the present composition (90.2% yield).

This preparation was subjected to an elemental analysis and to a two-dimensional development analysis utilizing electrophoresis and paper chromatography in the same way as described before. The constitution (molar ratio) thereof was SAM: sulfuric acid equivalent: 2'(3'),5'-UDS=1.00:1.43:1.31.

The results of the elemental analysis and the migration distances, R$_f$ values, and optical densities of SAM and 2'(3'),5'-UDS obtained by the two-dimensional development utilizing electrophoresis (1,000 V, 45 minutes) and paper chromatography are given below.

(Elemental analysis): C: 29.3%, H: 3.6%, N: 11.0%, S: 15.1% (moisture 1.89%).

(Two-dimensional development)
(220 γ of the present composition was spotted)
Distance of migration
SAM: 9.2 cm/45 min., 1,000 V
2'(3'),5'-UDS: −13.4 cm/45 min., 1,000 V
$R_f$ value
SAM: 0.35
2'(3'),5'-UDS: 0.62
Optical density
SAM: $OD_{257}=3.080$, $\epsilon=14700$
(in 0.1 N HCl): 0.210 μmole
2'(3'),5'-UDS: $OD_{260}=2.732$, $\epsilon=9900$
(in 0.1 N HCl): 0.276 μmole A certain quantity of the preparation was taken in a 3 ml ampule and dried under reduced pressure in the presence of phosphorus pentoxide. A preservation test (37° C.) was then conducted thereon in the same way as described before. The sample was found to be very stable as indicated in the following table.

TABLE 9

| Preservation days | 7 days | 14 days | 30 days |
|---|---|---|---|
| Percent residual SAM (%) | 97.0 | 99.6 | 100.2 |

REFERENCE EXAMPLE 2 (Preparation of 2'(3'),5'-UDS)

Into 10 ml of formamide and 5 ml of dimethylformamide was suspended with stirring 2.44 g of uridine, and 4.55 g of triethylamine-N-sulfonic acid was slowly added thereto. The reaction was continued for 3 hours at room temperature, after which the reaction mixture was poured into water to terminate the reaction.

The reaction mixture was adjusted to pH 6.5 with 1 N sodium hydroxide and, passed through a 200 ml column of Amberite IRA-402 (trade name, Rohm & Haas, U.S.A.) (Cl⁻ form) to effect adsorption, and then washed with water. The uridine-monosulfate fraction was eluted with 0.06 N hydrochloric acid from the column. The 2'(3')-5'-UDS fraction was then collected by elution with 0.4 M sodium chloride-0.005 N hydrochloric acid. The collected fraction was adjusted to pH 2.5 with 1 N hydrochloric acid, adsorbed on an activated charcoal column, washed with water, and then eluted with 0.02 N sodium hydroxide. The eluate was adjusted to pH 7.0 and concentrated, and then a threefold volume of ethanol was added thereto to precipitate white powder, which was dried in vacuo to obtain 1.45 g of uridine-2'(3'),5'-disulfate(2'(3'),5'-UDS).

EXAMPLE 6

In 80 ml of distilled water was dissolved 8.8 g of SAM hydrochloride obtained in the same way as in Example 5, after which neutralization (pH 7.0) was carried out in the same way as in Example 5. To the solution was added 6 ml of 12 N sulfuric acid. The mixture was added dropwise to 1,000 ml of ethanol, which was allowed to cool overnight. The resulting precipitate was filtered to obtain 9.6 g of SAM sulfate.

This SAM sulfate was dissolved in 100 ml of distilled water, and then 7.1 g of 2'(3'),5'-UDS obtained according to the process described in Reference Example 2 was added thereto. The resulting mixture was subjected to lyophilization (80 μm Hg, shelf temperature 25° C., 10 hours) to obtain 16.9 g of a preparation of the present composition.

With respect to this preparation, the same analysis and preservation test as in Example 5 were conducted, whereupon the results shown below were obtained.

(Constitution)
SAM:sulfuric acid equivalent:2'(3'),5'-UDS = 1.00:1.42:0.95; (Moisture 1.18%)
(Preservation stability, 37° C.)

TABLE 10

| Preservation days | 7 days | 14 days | 30 days |
|---|---|---|---|
| Percent residual SAM (%) | 96.2 | 94.0 | 98.0 |

EXAMPLE 7

In 100 ml of distilled water was dissolved 5.5 g of SAM sulfate obtained in the same way as in Example 6. Into the solution was further added and dissolved 10.1 g of 2'(3'),5'-UDS obtained according to the process set forth in Reference Example 2. Then, freeze-drying was carried out in the same way as in Example 6 to obtain 15.9 of a preparation of the present composition.

With respect to this preparation, the same analysis and preservation test as in Example 5 were conducted. The results are set forth below.

(Constitution)
SAM:sulfuric acid equivalent:2'(3'),5'-UDS = 1.00:1.42:2.39; (moisture 1.89%)
(Preservation Stability, 37° C.)

TABLE 11

| Preservation days | 7 days | 14 days | 30 days |
|---|---|---|---|
| Percent residual SAM (%) | 98.1 | 95.5 | 96.9 |

EXAMPLE 8

A commercially available baker's yeast (produced by Oriental Kobo Kagyo K. K., Japan) was cultivated on the Schlenk's medium [cf. the Journal of Biological Chemistry, Vol 229, 1037 (1957)] to accumulate SAM therein. The SAM was extracted with 25 liters of 1.5 N perchloric acid from 4.0 kgs. of the resulting baker's yeast with accumulated SAM, and thereafter the cell residue was removed by centrifugation.

To the extract thus treated was added potassium bicarbonate to adjust the pH to 5.5 and the resulting potassium perchlorate precipitate was removed. Then, 30 liters of the SAM solution thus treated was passed through a column of a weakly acidic cation exchange resin, Diaion WK 10 (trade name, manufactured by Mitsubishi Kasei Kogyo K. K., Japan) (H⁺ form) to cause SAM to be adsorbed thereon, after which elution with 0.1 N hydrochloric acid was carried out to obtain 10 liters of the SAM fraction. The eluate was concentrated to 400 ml under reduced pressure, the hydrochloric acid concentration of which was then adjusted to 0.1 N by means of a strongly basic anion exchange resin Dowex 2×8 (trade name, The Dow Chemical Company, USA) (Carbonic acid form). The eluate thus treated was added to 8 liters of a mixed solvent consisting of methanol and acetone (1:1) to obtain 24.5 g of SAM hydrochloride as a precipitate.

The SAM hydrochloride was dissolved in 300 ml of distilled water and neutralized to pH 7.0 with the Dowex 2×8 (carbonic acid form), and 23.5 ml of 12 N sulfuric acid was added thereto. The mixture was added to 6 liters of ethanol, which was allowed to cool overnight. The resulting precipitate was filtered and dried at a low temperature to obtain 30.1 g of SAM sulfate (moisture 5.4%).

Into 100 ml each of distilled water was dissolved 5.0 g each of the SAM sulfate, and then was dissolved therein 5'-IMS (free acid form), 5'-AMS sodium salt, 5'-GMS sodium salt or 5'-UMS (free acid form) (hereinafter referred to as 5'-IMS, 5'-AMS.Na, 5'-GMS.Na and 5'-UMS, respectively) which had been obtained according to the process in Reference Example 3 given below. The resulting solutions were subjected to freeze-drying (100 μm Hg or lower, shelf temperature 25° C., 10 hours) to obtain preparations of the present compositions comprising SAM, a sulfuric acid equivalent and 5'-IMS, 5'-AMS, 5'-GMS or 5'-UMS, these compositions hereinafter being referred to as 5'-IM composition, 5'-AM composition, 5'-GM composition, and 5'-UM composition, respectively.

In the following Table 12 are shown the species, and quantities added of the 5'-NMS used in the preparation as well as the yield quantities, water contents and yields of the preparations of the resulting compositions.

TABLE 12

| The present composition | 5'-NMS Species | Quantity used(g) | Yield (g) | Water content (%) | Yield (%) |
|---|---|---|---|---|---|
| 5'-IM composition | 5'-IMS | 2.79 | 7.32 | 1.5 | 96.0 |
| 5'-AM composition | 5'-AMS . Na | 2.96 | 7.39 | 1.2 | 95.0 |
| 5'-GM composition | 5'-GMS . Na | 3.08 | 7.99 | 1.9 | 87.0 |
| 5'-UM composition | 5'-UMS | 2.59 | 7.13 | 1.3 | 95.0 |

Results of analysis of each preparation of the present compositions described above are shown in the following tables. In Table 13 are shown the results obtained by spotting 300 γ of each preparation on a filter paper and subjecting it to two-dimensional dvelopment according to the above mentioned method and the molar quantity of each component calculated therefrom, whereby the electrophoretic and chromatographic properties of the preparations and the content of each component are determined. Table 14 shows the values of elemental analysis of each sample. Table 15 shows the constitution ratio (in molar ratio) of each component calculated from the resulting data.

TABLE 14

| Elemental analysis | 5'-IM Composition | 5'-AM Composition | 5'-GM Composition | 5'-UM Composition |
|---|---|---|---|---|
| C (%) | 31.6 | 31.2 | 31.3 | 31.4 |
| H (%) | 4.1 | 4.0 | 4.3 | 4.4 |
| N (%) | 14.4 | 16.0 | 16.1 | 13.7 |
| S (%) | 13.3 | 12.9 | 12.5 | 13.4 |

TABLE 15

| Constitution ratio (molar ratio) | 5'-IM Composition | 5'-AM Composition | 5'-GM Composition | 5'-UM Composition |
|---|---|---|---|---|
| SAM | 1.00 | 1.00 | 1.00 | 1.00 |
| Sulfuric acid equivalent | 1.74 | 1.79 | 1.68 | 1.71 |
| Corresponding NMS | 0.96 | 0.95 | 1.15 | 0.95 |

In order to test the stability in storage of the present compositions described above, 10 mg each of the preparation of each composition and 10 mg of SAM sulfate as a control were taken in 10 ml ampules respectively, and dried under reduced pressure in the presence of phosphorus pentoxide for 5 hours. The ampules were sealed and allowed to stand for the periods of 7, 14, and 30 days. The contents of SAM in the samples were then measured, and percent residual SAM was calculated. The results are shown in Table 16. As the control sample, SAM sulfate was subjected to lyophilization under reduced pressure (in the presence of phosphorus pentoxide).

TABLE 16

| Sample | Preservation days | | |
|---|---|---|---|
| | 7 days | 14 days | 30 days |
| Control | 82.4% | 77.9% | 66.7% |
| 5'-IM Composition | 99.8% | 98.5% | 98.5% |
| 5'-AM Composition | 97.3% | 93.8% | 90.4% |
| 5'-GM Composition | 98.6% | 94.4% | 91.6% |
| 5'-UM Composition | 99.0% | 96.4% | 95.5% |

EXAMPLE 9

SAM hydrochloride obtained in the same way as in Example 8 was dissolved in distilled water to obtain 100 ml of 10% SAM solution. The solution was adjusted to pH 7.0 with a strongly basic anion exchange resin Dowex 2×8 (carbonic acid type), and then 12.5 ml of 12 N sulfuric acid and 53.734 g of 5'-IMS free acid form (moisture 2.8%) were added thereto.

TABLE 13

| | 5'-IM Composition | | 5'-AM Composition | | 5'-GM Composition | | 5'-UM Composition | |
|---|---|---|---|---|---|---|---|---|
| | SAM | 5'-IMS | SAM | 5'-AMS | SAM | 5'-GMS | SAM | 5'-UMS |
| Electrophoresis migration distance (cm/50min.,1,000V) | 8.8 | −4.2 | 8.5 | −0.5 | 9.0 | −3.9 | 8.6 | −3.5 |
| Paper chromatography (Rf) | 0.35 | 0.59 | 0.35 | 0.57 | 0.35 | 0.48 | 0.35 | 0.64 |
| 0.1N HCl (nm) λmax | 257 | 250 | 257 | 256 | 257 | 255 | 257 | 260 |
| Optical density | 4.91 | 3.93 | 4.789 | 4.690 | 4.384 | 4.031 | 5.143 | 3.307 |
| ε | 14700 | 12200 | 14700 | 15100 | 14700 | 11800 | 14700 | 9900 |
| Molar quantity (μmole) | 0.334 | 0.322 | 0.326 | 0.311 | 0.298 | 0.342 | 0.350 | 0.334 |

The resulting solution was added dropwise to 2.0 liters of ethanol, which was allowed to cool overnight. The resulting precipitate was filtered and dried at a low temperature to obtain 24.8 g of a preparation of 5'-IM composition (moisture 2.8%, yield 92.2%).

This preparation was analysed in the same way as in Example 8 to determine the constitution ratio of SAM:-sulfuric acid equivalent:5'-IMS = 1.00:1.48:1.36.

| Elemental analysis | | | |
|---|---|---|---|
| C | 32.4%, | H | 4.1% |
| N | 14.9%, | S | 11.9% |

The quantities of components (molar quantities)
The optical densities were measured as shown below by separation of 300 γ of the preparation of the present composition by means of two-dimensional development.

SAM: $OD_{257nm} = 4.294$; 0.292 μmole
5'-IMS: $OD_{250nm} = 4.833$; 0.396 μmole With respect to this preparation, the same preservation test (37° C.) as in Example 8 was conducted, whereupon it was found to be very stable as indicated in the following table.

TABLE 17

| Preservation days | 7 days | 14 days | 30 days |
|---|---|---|---|
| Percent residual SAM (%) | 100.9 | 98.2 | 97.2 |

EXAMPLE 10

SAM hydrochloride obtained in the same way as in Example 8 was dissolved in distilled water to obtain 20 ml of 10% SAM solution. The solution was neutralized to pH 7.0 in the same way as in Example 8, and then 2.5 ml of 12 N sulfuric acid and 6.30 g of 5'-GMS sodium salt (moisture 8.3%) were added thereto. The resulting mixture was added dropwise to 400 ml of ethanol, which was allowed to cool overnight. The resulting precipitate was filtered and then dried at a low temperature to obtain 5.79 g of a preparation of 5'-GM composition (moisture 2.2%, yield 91.1%).

This preparation was analysed in the same way as in Example 8 to determine the constitution ratio of SAM:-sulfuric acid equivalent:5'-GMS = 1.00:1.45:1.93. The preservation stability at 50° C. of the preparation was compared with that of the conventional SAM sulfate, whereupon the result shown in the following table was obtained. The values given in Table 18 stand for percent residual SAM (%).

TABLE 18

| | Preservation days | | |
|---|---|---|---|
| Sample | 7 days | 14 days | 30 days |
| 5'-GM Composition | 92.6 | 85.5 | 78.5 |

TABLE 18-continued

| | Preservation days | | |
|---|---|---|---|
| Sample | 7 days | 14 days | 30 days |
| SAM sulfate | 61.8 | 54.1 | 43.9 |

EXAMPLE 11

In 100 ml each of distilled water was dissolved 5.0 g each of SAM sulfates obtained in the same way as in Example 8. In the resulting solutions were dissolved 3'-TMS (free acid form), 2'(3')-AMS sodium salt, 2'(3')-CMS sodium salt and 2'(3')-UMS (free acid form) (hereinafter referred to as 3'-TMS, 2'(3')-AMS.Na, 2'(3')-CMS.Na and 2'(3')-UMS), respectively, which had been obtained according to the process in Reference Example 4 set forth below. The resulting solutions were subjected to freeze-drying (100 μm Hg or lower, shelf temperature 25° C., 10 hours) to obtain preparations of the present compositions comprising SAM, a sulfuric acid equivalent and 3'-TMS, 2'(3')-AMS, 2'(3')-CMS or 2'(3')-UMS (these compositions being hereinafter referred to as 3'-TM composition, 2'(3')-AM composition, 2'(3')-CM composition and 2'(3')-UM composition, respectively).

In the following Table 19 are shown the species and amounts added of the 3'- or 2'(3')-NMS used in the preparation as well as the yield quantities, water contents, and yields of the preparations of the resulting compositions.

TABLE 19

| | 3'-or 2'(3')-NMS | | Used yield (g) | Water content (%) | Yield (%) |
|---|---|---|---|---|---|
| The present composition | Species | quantity used (g) | | | |
| 3'-TM composition | 3'-TMS | 2.69 | 7.40 | 1.6 | 98.2 |
| 2'(3')-AM composition | 2'(3')-AMS . Na | 4.54 | 9.33 | 1.4 | 99.2 |
| 2'(3')-CM composition | 2'(3')-CMS Na | 5.69 | 10.48 | 1.8 | 98.8 |
| 2'(3')-UM composition | 2'(3') UMS | 5.38 | 10.11 | 2.3 | 97.7 |

Results of analysis of each preparation of the present compositions described above are shown in the following tables. In Table 20 are shown the results obtained by spotting 300 γ of each preparation on a filter paper and subjecting it to two-dimensional development according to the above-mentioned method and the molar quantity of each component calculated therefrom, whereby the electrophoretic and chromatographic properties of the preparations and the content of each component are determined. Table 21 shows the results of elemental analysis of each samples. Table 22 shows the constitution ratio (molar ratio) of each component which was calculated from the above mentioned results and the sulfur contents determined by an oxygen-flask combustion method.

TABLE 20

| | 3'-TM Composition | | 2'(3')-AM Composition | | 2'(3')-CM Composition | | 2'(3')-UM Composition | |
|---|---|---|---|---|---|---|---|---|
| | SAM | 3'-TMS | SAM | 2'(3')-AMS | SAM | 2'(3')-CMS | SAM | 2'(3')-UMS |
| Electrophoresis migration distance (cm/45 min., 1000V) | 9.6 | −4.0 | 9.0 | −0.3 | 10.1 | 0.4 | 11.5 | −6.3 |
| Paper chromatography (Rf) | 0.29 | 0.89 | 0.26 | 0.85 | 0.28 | 0.72 | 0.32 | 0.87 |

TABLE 20-continued

|  | 3'-TM Composition | | 2'(3')-AM Composition | | 2'(3')-CM Composition | | 2'(3')-UM Composition | |
| --- | --- | --- | --- | --- | --- | --- | --- | --- |
|  | SAM | 3'-TMS | SAM | 2'(3')-AMS | SAM | 2'(3')-CMS | SAM | 2'(3')-UMS |
| 0.1 N HCl |  |  |  |  |  |  |  |  |
| λmax (nm) | 257 | 267 | 257 | 256 | 257 | 280 | 257 | 262 |
| Optical density | 4.792 | 3.168 | 3.851 | 6.010 | 3.410 | 5.920 | 3.499 | 4.683 |
| ε | 14700 | 9600 | 14700 | 15100 | 14700 | 12700 | 14700 | 9900 |
| Molar quantity (μmole) | 0.326 | 0.330 | 0.262 | 0.398 | 0.232 | 0.466 | 0.238 | 0.473 |

TABLE 21

| Elemental analysis | 3'-TM Composition | 2'(3')-AM Composition | 2'(3')-CM Composition | 2'(3')-UM Composition |
| --- | --- | --- | --- | --- |
| C (%) | 33.31 | 31.31 | 33.92 | 84.81 |
| H (%) | 4.31 | 4.15 | 4.46 | 4.50 |
| N (%) | 12.20 | 16.28 | 14.22 | 12.31 |

TABLE 22

|  | 3'-TM Composition | 2'(3')-AM Composition | 2'(3')-CM Composition | 2'(3')-UM Composition |
| --- | --- | --- | --- | --- |
| SAM | 1.00 | 1.00 | 1.00 | 1.00 |
| Sulfuric acid equivalent | 1.80 | 1.79 | 1.77 | 1.84 |
| Corresponding NMS | 1.01 | 1.52 | 2.01 | 1.99 |

The stabilities in storage of the present compositions described above were tested in the same way as in Example 8. The results are shown in Table 23.

TABLE 23

| Sample | Preservation days | | |
| --- | --- | --- | --- |
|  | 7 days | 14 days | 30 days |
| Control | 82.4% | 77.9% | 66.7% |
| 3'-TM Composition | 100% | 100% | 99.8% |
| 2'(3')-AM Composition | 99.1% | 100% | 98.2% |
| 2'(3')-CM Composition | 97.7% | 97.7% | 96.5% |
| 2'(3')-UM Composition | 100% | 89.9% | 93.2% |

EXAMPLE 12

In 100 ml each of distilled water was dissolved 5.0 g each of the SAM sulfates (moisture 5.8%) obtained in the same way as in Example 8. In the resulting solutions, were dissolved 2'(3')-CDS disodium salt, 2'(3'),5'-ADS disodium salt, 2'(3'-IDS (free acid form), 2'(3'), 5'-GDS disodium salt, 2',3'-ADS disodium salt, 2',3'-CDS disodium salt, 2',3'-UDS (free acid form) and 3',5'-TDS disodium salt (hereinafter referred to as 2'(3'), 5'-CDS.2Na, 2'(3'), 5'-ADS.2Na, 2'(3'),5'-IDS, 2'(3'),5'-GDS.2Na, 2', 3'-ADS.2Na, 2', 3'-CDS.2Na, 2', 3'-UDS and 3',5'-TDS.2Na), respectively, which had ben obtained according to the process shown in Reference Example 5 given below. The resulting solutions were subjected to lyophilization (100 μm Hg or lower shelf temperature 25° C., 10 hours) to obtain preparations of the present compositions comprising SAM, sulfuric acid equivalent, and 2'(3'),5'-CDS, 2'(3'),5'-ADS, 2'(3'),5'-IDS, 2'(3'),5'-GDS, 2', 3'-ADS, 2', 3'-CDS, 2', 3'-UDS or 3', 5'-TDS (hereinafter these compositions being referred to as 2'(3'),5'-CD composition, 2'(3'), 5'-AD composition, 2'(3'), 5'-ID composition, 2'(3'), 5'-GD composition, 2', 3'-AD composition, 2', 3'-CD composition, 2', 3'-UD composition, 3', 5'-TD compositions, respectively).

In the following Table 24 are shown the species and quantities added of the NDS used in the preparations as well as the yield quantities, water contents, and yields of the preparations of the resulting compositions.

TABLE 24

| Present composition | NDS | | Yield (g) | Water content (%) | Yield(%) |
| --- | --- | --- | --- | --- | --- |
|  | Species | Quantity (g) |  |  |  |
| 2'(3'),5'-CD composition | 2'(3'),5'-CDS . 2Na | 5.43 | 9.99 | 1.0 | 97.5 |
| 2'(3'),5'-AD composition | 2'(3'),5'-ADS . 2Na | 3.82 | 8.44 | 0.8 | 98.1 |
| 2'(3'),5'-ID composition | 2'(3'),5'-IDS | 3.47 | 7.98 | 0.7 | 96.9 |
| 2'(3'),5'-GD composition | 2'(3'),5'-GDS . 2Na | 3.95 | 8.46 | 1.1 | 96.6 |
| 2',3'-AD composition | 2',3'-ADS . 2Na | 3.82 | 8.43 | 1.1 | 97.7 |
| 2',3'-CD composition | 2',3'-CDS . 2Na | 3.62 | 8.30 | 0.8 | 98.8 |
| 2',3'-UD composition | 2',3'-UDS | 3.27 | 7.76 | 1.8 | 95.5 |
| 3',5'-TD composition | 3',5'-TDS . 2Na | 7.22 | 11.71 | 0.6 | 97.6 |

Results of analysis of each preparation of the present compositions described above are shown in the following tables. In Tables 25(a) and 25(b) are shown the results obtained by spotting 300 γ of each preparation on a filter paper and subjecting it to two-dimensional development according to the above-mentioned method, whereby the electrophoretic and chromatographic properties of the preparations and the content of each component were determined, the molar quantity of each component calculated therefrom, the values of elemental analysis, and the constitution ratio (molar ratio) of each component.

TABLE 25(a)

| The present composition | 2'(3'),5'-CD composition | | 2'(3'),5'-AD composition | | 2'(3'),5'-ID composition | | 2'(3'),5'-GD composition | |
| --- | --- | --- | --- | --- | --- | --- | --- | --- |
|  | SAM | 2'(3'),5'-CDS | SAM | 2'(3'),5' ADS | SAM | 2'(3'),5'-IDS | SAM | 2'(3'),5'-GDS |
| Electrophoresis migration distance (cm/45min., 1000V) | 9.0 | −2.0 | 9.5 | −4.8 | 10.1 | −5.7 | 9.8 | −5.0 |

TABLE 25(a)-continued

| The present composition | | 2'(3'),5'-CD composition | | 2'(3'),5'-AD composition | | 2'(3'),5'-ID composition | | 2'(3'),5'-GD composition | |
|---|---|---|---|---|---|---|---|---|---|
| | | SAM | 2'(3'),5'-CDS | SAM | 2'(3'),5'-ADS | SAM | 2'(3'),5'-IDS | SAM | 2'(3'),5'-GDS |
| Paper chromatography (Rf) 0.1N HCl | | 0.32 | 0.77 | 0.30 | 0.80 | 0.30 | 0.89 | 0.33 | 0.81 |
| λmax (nm) | | 257 | 280 | 257 | 257 | 257 | 249 | 257 | 255 |
| Optical density | | 3.499 | 4.559 | 4.160 | 4.261 | 4.351 | 3.582 | 4.087 | 3.550 |
| ε | | 14700 | 12700 | 14700 | 14900 | 14700 | 12100 | 14700 | 12500 |
| molar quantity (μmole) | | 0.238 | 0.359 | 0.283 | 0.286 | 0.296 | 0.296 | 0.278 | 0.284 |
| Elemental analysis | C (%) | 27.14 | | 28.38 | | 29.85 | | 27.99 | |
| | H (%) | 3.50 | | 3.59 | | 3.91 | | 3.60 | |
| | N (%) | 11.58 | | 14.45 | | 13.82 | | 14.21 | |
| | S (%) | 14.71 | | 14.71 | | 15.22 | | 14.15 | |
| Constitution ratio (molar ratio) | SAM | 1.00 | | 1.00 | | 1.00 | | 1.00 | |
| | Sulfuric acid equivalent | 1.80 | | 1.85 | | 1.78 | | 1.84 | |
| | Corresponding NDS | 1.51 | | 1.01 | | 1.00 | | 1.02 | |

TABLE 25(b)

| The present composition | | 2',3'-AD composition | | 2',3'-CD composition | | 2',3'-UD composition | | 3',5'-TD composition | |
|---|---|---|---|---|---|---|---|---|---|
| | | SAM | 2',3'-ADS | SAM | 2',3'-CDS | SAM | 2',3'-UDS | SAM | 3',5'-TDS |
| Electrophoresis migration distance (cm/45 min., 1000V) | | 10.1 | −3.9 | 9.6 | −4.3 | 10.6 | −6.3 | 9.0 | −4.3 |
| Paper chromatography (Rf) 0.1N HCl | | 0.30 | 0.83 | 0.32 | 0.82 | 0.34 | 0.87 | 0.29 | 0.90 |
| λmax (nm) | | 257 | 257 | 257 | 280 | 257 | 262 | 257 | 267 |
| Optical density | | 4.145 | 4.298 | 4.263 | 3.937 | 4.410 | 3.119 | 2.969 | 3.859 |
| ε | | 14700 | 14900 | 14700 | 12700 | 14700 | 9900 | 14700 | 9600 |
| molar quantity (μmole) | | 0.282 | 0.307 | 0.290 | 0.310 | 0.300 | 0.315 | 0.202 | 0.402 |
| Elemental analysis | C (%) | 28.08 | | 27.98 | | 28.94 | | 28.60 | |
| | H (%) | 3.66 | | 3.68 | | 3.92 | | 3.20 | |
| | N (%) | 14.45 | | 12.10 | | 11.01 | | 9.48 | |
| | S (%) | 14.46 | | 14.79 | | 15.29 | | 14.81 | |
| Constitution ratio molar ratio | SAM | 1.00 | | 1.00 | | 1.00 | | 1.00 | |
| | Sulfuric acid equivalent | 1.84 | | 1.81 | | 1.84 | | 1.79 | |
| | Corresponding NDS | 1.09 | | 1.07 | | 1.05 | | 1.99 | |

In order to test the stability in storage of the present compositions described above, 10 mg each of the preparation of each composition and 10 mg of SAM sulfate as a control were taken in 10 ml ampules respectively, and dried under reduced pressure in the presence of phosphorus pentoxide for 5 hours. The ampules were sealed and allowed to stand for the periods of 7, 14 and 30 days. The contents of SAM in the samples were then measured, and percent residual SAM was calculated. The results are shown in Table 26. As the control sample, SAM sulfate was subjected to freeze-drying and drying under reduced pressure (in the presence of phosphorus pentoxide).

TABLE 26

| Sample | Preservation days | | |
|---|---|---|---|
| | 7 days | 14 days | 30 days |
| Control | 82.4% | 77.9% | 66.7% |
| 2'(3'),5'-CD Composition | 100% | 97.7% | 96.5% |
| 2'(3'),5'-AD Composition | 100% | 99.2% | 98.7% |
| 2'(3'),5'-ID Composition | 98.2% | 94.3% | 90.6% |
| 2'(3'),5'-GD Composition | 96.6% | 92.2% | 90.1% |
| 2',3'-AD Composition | 100% | 91.4% | 91.1% |
| 2',3'-CD Composition | 97.1% | 95.5% | 92.8% |
| 2',3'-UD Composition | 100% | 95.1% | 97.6% |

TABLE 26-continued

| Sample | Preservation days | | |
|---|---|---|---|
| | 7 days | 14 days | 30 days |
| Control | 82.4% | 77.9% | 66.7% |
| 3',5'-TD Composition | 99.3% | 100% | 95.3% |

REFERENCE EXAMPLE 3 (preparation of 5'-NMS)

In a mixture of 200 ml formaldehyde and 100 ml dimethylformamide, 200 m moles of a nucleoside (inosine, adenosine, guanosine and uridine) corresponding to 5'-NMS to be prepared was suspended with stirring, after which 400 m moles of triethylamine-N-sulfonic acid was added slowly thereto. Reaction was carried out at room temperature for 3 hours in the case of 5'-AMS, 5 hours in the case of 5'-GMS, and 0.5 hour in the case of the other 5'-NMS, respectively. The reaction mixture was then poured into water to terminate the reaction.

Thereafter, the reaction mixture was adjusted to pH 6.5 with 1 N sodium hydroxide and then passed through a 4-liter column of Amberite IRA-402 (trade name, manufactured by Rohm & Haas Company, U.S.A.) (Cl⁻ form) to effect adsorption, which was followed by washing with water and then elution with 0.04 N hydrochloric acid. The resulting 5'-NMS fraction was collected, adjusted to pH 5.7 with 1 N sodium hydroxide, and concentrated. Then a three-fold quantity of acetone was added thereto to precipitate crystals, which were dried in vacuo to obtain the corresponding 5'-NMS. The yields in the above described processes were: 5'-IMS sodium salt 57.7%, 5'-AMS sodium salt 67.1%, 5'-GMS sodium salt 73.9%, and 5'-UMS sodium salt 63.7%, respectively.

The resulting 5'-AMS and 5'-GMS sodium salts were used without further treatment, for the production of the present compositions. In the case of 5'-IMS sodium salt 5'-UMS sodium salt, however, the aqueous solution thereof was prepared and passed through a column of Diaion PK 216 (trade name, manufactured by Mitsubishi Kasei Kogyo K.K., Japan) to convert the sodium salt to free acid form, which was then used for the production of the present composition.

REFERENCE EXAMPLE 4 (preparation of 3'-or 2'(3')-NMS)

In 40 ml of pyridine was suspended with stirring 20 m moles of a 5'-O-trityl nucleoside (tritylthymidine, tritylatadenosine, tritylcytidine and trityluridine) corresponding to 3'-or 2'(3')-NMS to be prepared. To the mixture was slowly added 60 m moles of triethylamine-N-sulfonic acid, and the mixture was allowed to stand overnight to cause a reaction, which was followed by pouring the reaction mixture into water to terminate the reaction.

The resulting 5'-O-trityl NMS was then extracted from the reaction mixture with n-butanol. The organic solvent layer was washed with water and concentrated to dryness. The resulting residue was dissolved in 200 ml of a solution of chloroform and formic acid (1:1), and the solution was allowed to stand for 10 minutes at room temperature to remove the trityl group from the NMS.

In the preparation of 2'(3')-CMS or 2'(3')-UMS, the solution after the detritylation was concentrated to dryness, dissolved in water, and adjusted to pH 6.5 with 1N sodium hydroxide. Then the formed insoluble triphenyl carbinol was removed. The resulting solution was treated with Amberite IRA-402 in the same way as in Reference Exanple 3. Crystals were precipitated with ethanol and dried under vacuum to obtain the corresponding 2'(3')-NMS sodium salt. The yields in the above described processes were 2'(3')-AMS sodium salt 41.7%, 2'(3')-CMS sodium salt 44.5%, and 2'(3')-UMS sodium salt 58.6%, respectively.

In the preparation of 3'-TMS, the solution after the detritylation was adsorbed on 200 ml activated charcoal, washed with water, and eluted with a mixture of ethanol, amonia, and water (50:2:48). The resulting TMS fraction was collected, concentrated to dryness, and dissolved in 300 ml of water, The solution was passed through a column of Diaion PK 216 (H+ form), neutralized with sodium hydroxide, and crystallized with ethanol (yield 73.2%).

The resulting 2'(3')-AMS and 2'(3')-CMS sodium salts were used, without further treatment, for the production of present compositions. In case of 3'-TMS sodium salt or 2'(3')-UMS sodium salt, however, the aqueous solution thereof was prepared and passed through a column of Diaion PK 216 to convert the sodium salt to free acid form, which was then used for the production of a present composition.

REFERENCE EXAMPLE 5 (Preparation of 2'(3'),5'- or 3,5'-NDS)

In a mixture of 20 ml formamide and 10 ml dimethylformamide was suspended with stirring 20 m moles of a nucleoside (cytidine, adenosine, inosine, guanosine and thymidine) corresponding to 2'(3'),5'- or 3',5'-NDS. To this mixture was slowly added 40 m moles of triethylamine-N-sulfonic acid. Reaction was carried out at room temperature for 6 hours in the case of 2'(3'),5'-ADS, 24 hours in the case of 2'(3'),5'-GDS, and 3 hours in the case of the other NDS, respectively. The reaction mixture was then poured into water to terminate the reaction.

Thereafter, the reaction mixture was adjusted to pH 6.5 with 1 N sodium hydroxide and then passed through a 400 ml column of Amberite IRA-402 (trade name, manufactured by Rohm & Hass Company, U.S.A.) (Cl⁻ form) to carry out adsorption, which was followed by washing with water. Nucleoside-5'-monosulfate fraction was eluted with 0.04 N hydrochloric acid and removed. The NDS fraction was then eluted with a mixed solution of 0.2 M sodium chloride-0.05 N hydrochloric acid and collected.

The collected eluate was adjusted to pH 1.5, adsorbed on a 600 ml activated charcoal column, washed with water, eluted with 0.1 N ammonia water, and desalted. The resulting solution was concentrated, adjusted to pH 10 with 1 N sodium hydroxide, concentrated again to make the NDS concentration 30 to 50%. The resulting solution was adjusted to pH 8.0 to 10.0, and a 3-to 5-fold volume of ethanol was added thereto with stirring to precipitate crystals, which were then dried under vocuum to obtain the corresponding NDS disodium salt. The yields in the above described processes were: 2'(3'),5'-IDS disodium salt 49%, 2'(3').5'-ADS disodium salt 52%, 2'(3'), 5'-CDS disodium salt 58%, 2'(3'),5'-GDS disodium salt 45%, 3',5'-TDS disodium salt 62%, respectively.

REFERENCE EXAMPLE 6 (Preparation of 2',3'-NDS)

In 40 ml of pyridine was suspended with stirring 20 m moles of a 5'-O-trityl nucleoside (tritylatadenosine, tritylcytidine and trityluridine) corresponding to 2',3'-NDS to be prepared. To this mixture was slowly added triethylamine-N-sulfonic acid (60 m moles in the case of tritylatadenosine or tritylcytidine, and 120 m moles in the case of trityluridine) and allowed to stand overnight to cause reaction, which was followed by pouring of the reaction mixture into water to terminate the reaction.

The resulting 5'-O-trityl NDS was then extracted from the reaction mixture with n-butanol. The organic solvent layer was washed with a small quantity of water and concentrated to dryness. The resulting residue was dissolved in 200 ml of a solution of chloroform and formic acid (1:1), and the solution was allowed to stand for 10 minutes at room temperature to cause detritylation (removal of trityl group from the NDS). The resulting solution was concentrated to dryness, dissolved in water, adjusted to pH 6.5 with 1 N sodium hydroxide, after which the formed insoluble triphenyl carbinol was filtered off therefrom. The resulting solution was then treated with Amberite IRA-402 in the same way as in Reference Example 5. The NDS fraction was concentrated and then crystallized with ethanol to obtain 2',3'-NDS. The yields in the above-mentioned processes were 50.3% for 2′,3′-ADS.2Na, 35.1% for 2′,3′-CDS.2Na and 84.1% for 2′,3′-UDS.2Na, respectively.

The resulting 2′,3′-ADS.2Na and 2′,3′-CDS.2Na were used, without further treatment, for the production of present compositions. In the case of 2′, 3′-UDS.2Na, however, the aqueous solution thereof was prepared and passed through a column of Diaion PK 216 to convert the disodium salt to free acid form, which was then used for the production of the present composition.

What we claim is:

1. An S-adenosyl-L-methionine composition stabilized against decomposition of S-adenosyl-L-methionine comprising S-adenosyl-L-methionine, a sulfuric acid equivalent, and a nucleoside sulfate.

2. The composition as set forth in claim 1, in which the molar ratio of the components is 1 part of S-adenosyl-L-methionine to from 1 to 3 parts of the sulfuric acid equivalent to not less than 0.5 part of the nucleoside sulfate.

3. The composition as set forth in claim 1, in which the nucleoside sulfate is a member selected from the group consisting of a nucleoside monosulfate, a nucleoside disulfate, and mixtures thereof.

4. The composition as set forth in claim 3, in which the nucleoside monosulfate is a member selected from the group consisting of inosine-5′-monosulfate, adenosine-5′-monosulfate, guanosine-5′-monosulfate, uridine-5′-monosulfate, cytidine-5′-monosulfate, xanthosine-5′-monosulfate, thymidine-5′-monosulfate, deoxyguanosine-5′-monosulfate, deoxyinosine-5′-monosulfate, inosine-2′(3′)-monosulfate, adenosine-2′(3′)-monosulfate, guanosine-2′(3′)-monosulfate, cytidine-2′(3′)-monosulfate, uridine-2′)3′)-monosulfate, thymidine-3′-monosulfate, deoxyinosine-3′-monosulfate, deoxyadenosine-3′-monosulfate, deoxyguanosine-3′-monosulfate, deoxycytidine-3′-monosulfate, and mixtures thereof.

5. The composition as set forth in claim 3, in which the nucloside disulfate is a member selected from the group consisting of inosine-2′(3′),5′-disulfate, adenosine-2′(3′),5′-disulfate, guanosine-2′(3′),5′-disulfate, xanthosine-2′(3′),5′-disulfate, uridine-2′(3′),5′-disulfate, cytidine-2′(3′),5′-disulfate, thymidine-3′,5′-disulfate, deoxyinosine-3′,5′-disulfate, deoxyadenosine-3′,5′-disulfate, deoxyguanosine-3′,5′-disulfate deoxyxanthosine-3′,5′-disulfate, deoxycytidine-3′,5′-disulfate, adenosine-2′,3′-disulfate, inosine-2′,3′-disulfate, guanosine-2′,3′-disulfate, xanthosine-2′,3′-disulfate, cytidine-2′,3′-disulfate, uridine-2′,3′-disulfate, and mixtures thereof.

6. The composition as set forth in claim 2, in which the nucleoside sulfate is a member selected from the group consisting of a nucleoside monosulfate, a nucleoside disulfate, and mixtures thereof.

7. The composition as set forth in claim 6, in which the nucleoside monosulfate is a member selected from the group consisting of inosine-5′-monosulfate, adenosine-5′-monosulfate, guanosine-5′-monosulfate, uridine-5′-monosulfate, cytidine-5′-monosulfate, xanthosine-5′-monosulfate, thymidine-5′-monosulfate, deoxyguanosine-5′-monosulfate, deoxyinosine-5′-monosulfate, inosine-2′(3′)-monosulfate, adenosine-2′(3′)-monosulfate, guanosine-2′(3′)-monosulfate, cytidine-2′(3′)-monosulfate, uridine-2′(3′)-monosulfate, thymidine-3′-monosulfate, deoxyinosine-3′-monosulfate, deoxyadenosine-3′-monosulfate, deoxyguanosine-3′-monosulfate, deoxycytidine-3′-monosulfate, and mixtures thereof.

8. The composition as set forth in claim 6, in which the nucloside disulfate is a member selected from the group consisting of inosine-2′(3′),5′-disulfate, adenosine-2′(3′),5′-disulfate, guanosine-2′(3′),5′-disulfate, xanthosine-2′(3′),5′-disulfate, uridine-2′(3′),5′-disulfate, cytidine-2′(3′),5′-disulfate, thymidine-3′,5′-disulfate, deoxyinosine-3′,5′-disulfate, deoxyadenosine-3′,5′-disulfate, deoxyguanosine-3′,5′-disulfate, deoxyxanthosine-3′,5′-disulfate, deoxycytidine-3′,5′-disulfate, adenosine-2′,3′-disulfate, inosine-2′,3′-disulfate, guanosine-2′,3′-disulfate, xanthosine-2′,3′-disulfate, cytidine-2′,3′-disulfate, uridine-2′,3′-disulfate, and mixtures thereof.

* * * * *